(12) United States Patent
Rustad et al.

(10) Patent No.: US 7,614,420 B2
(45) Date of Patent: Nov. 10, 2009

(54) AUTOFEED MECHANISM FOR HEATED HUMIDIFIER CHAMBER

(75) Inventors: Andre Rustad, Etiwanda, CA (US); Scott Halperin, Orange, CA (US)

(73) Assignee: Allegiance Corporation, McGaw Park, IL (US)

( * ) Notice: Subject to any disclaimer, the term of this patent is extended or adjusted under 35 U.S.C. 154(b) by 345 days.

(21) Appl. No.: 11/405,341

(22) Filed: Apr. 17, 2006

(65) Prior Publication Data
US 2007/0240767 A1 Oct. 18, 2007

(51) Int. Cl.
*F16K 31/18* (2006.01)
(52) U.S. Cl. ............................... 137/430; 137/423
(58) Field of Classification Search ................ 137/423, 137/426, 429, 430
See application file for complete search history.

(56) References Cited

U.S. PATENT DOCUMENTS

| | | | | |
|---|---|---|---|---|
| 1,968,293 A | * | 7/1934 | Gould | 73/198 |
| 2,603,493 A | * | 7/1952 | Rusconi | 137/202 |
| 2,904,062 A | * | 9/1959 | Techler | 137/391 |
| 3,095,005 A | * | 6/1963 | Thompson | 137/268 |
| 3,185,302 A | * | 5/1965 | Kryzer | 210/126 |
| 3,230,970 A | * | 1/1966 | Smith | 137/432 |
| 6,238,567 B1 | * | 5/2001 | Van de Moortele | 210/670 |
| 6,551,504 B2 | * | 4/2003 | Reed | 210/97 |

* cited by examiner

*Primary Examiner*—John Rivell
*Assistant Examiner*—Atif H Chaudry
(74) *Attorney, Agent, or Firm*—Dicke, Billig & Czaja, PLLC

(57) ABSTRACT

An autofeed mechanism for controlling the flow and level of a fluid. The mechanism includes a body with an inlet chamber and a float chamber. A seat permits fluid communication between the two chambers. A float and a ball cooperate to permit, or deny, access to the seat. Fluid first enters the inlet and fills the chamber and then enters the float chamber by passing through the seat and exiting via the exit. Initially, the weight of the float keeps the ball away from the seat, but eventually the fluid level rises high enough that the action of the float on the ball decreases to a level that is overcome by the buoyant force of the ball and other fluidic forces resulting in the ball moving away from the ball support. Finally, the ball rises enough to seal against the seat thus stopping the flow of fluid.

21 Claims, 14 Drawing Sheets

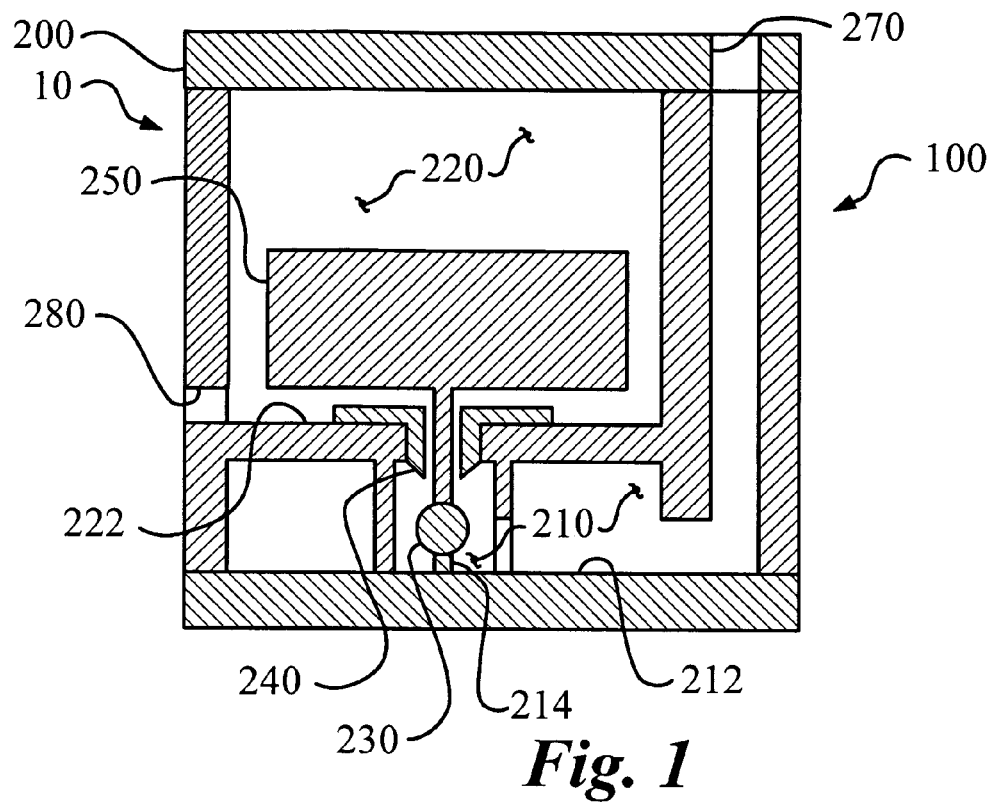
Fig. 1
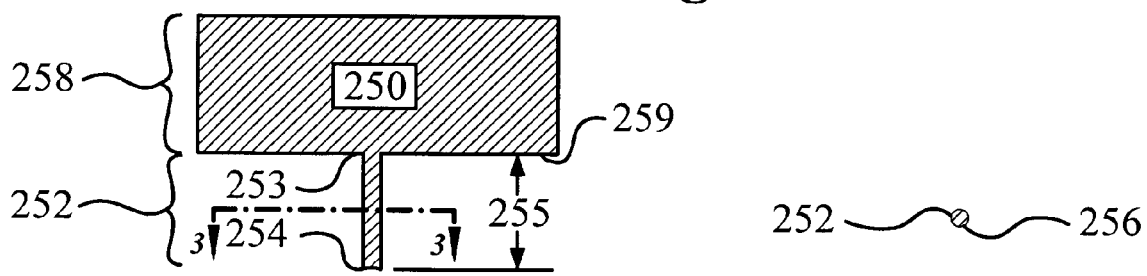
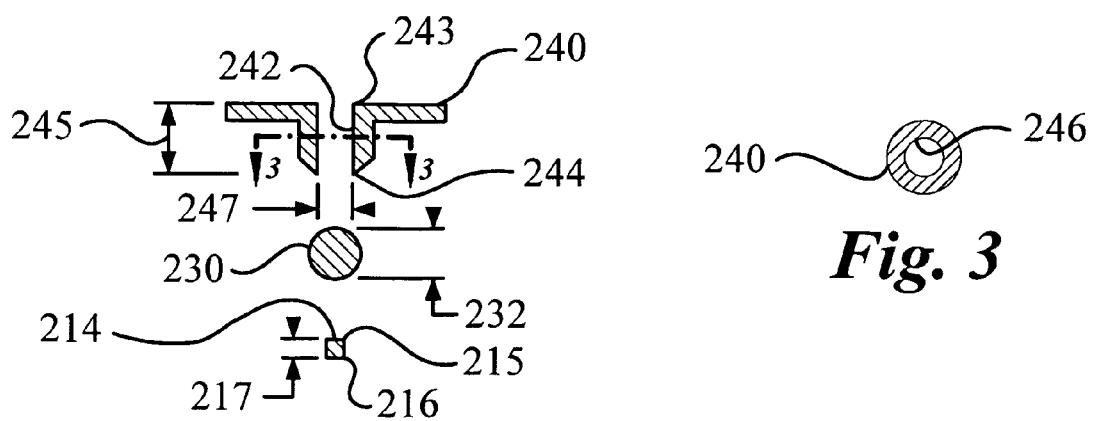
Fig. 2
Fig. 3

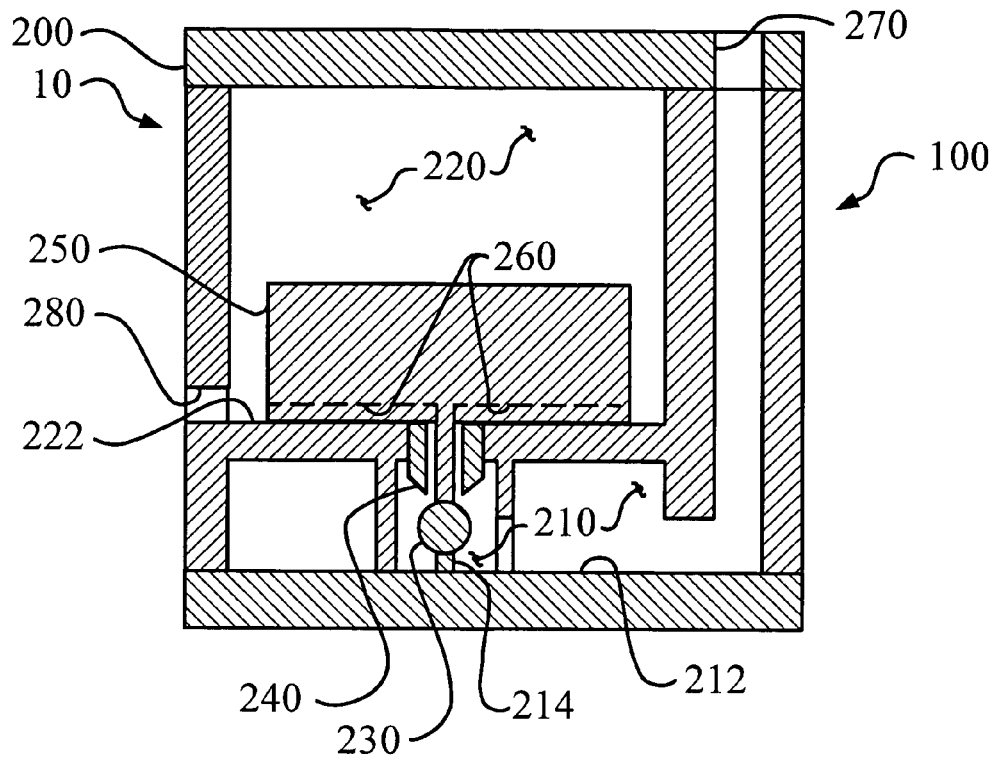
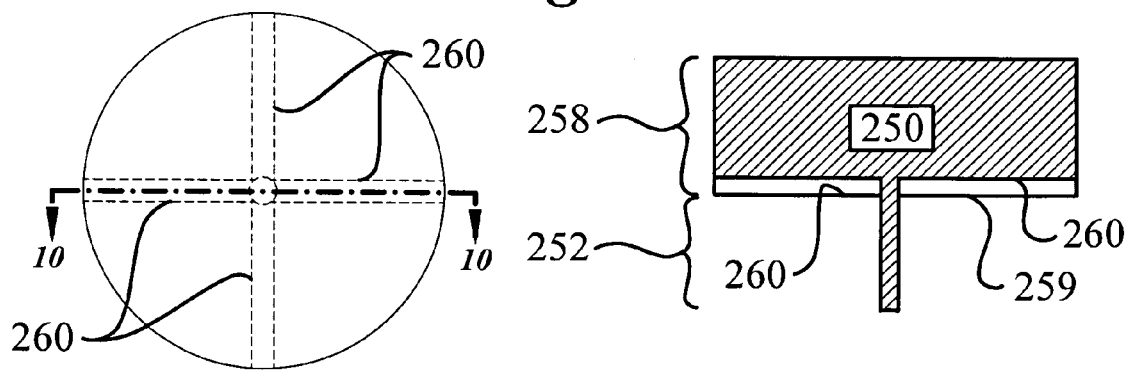
*Fig. 8*
*Fig. 9*  *Fig. 10*

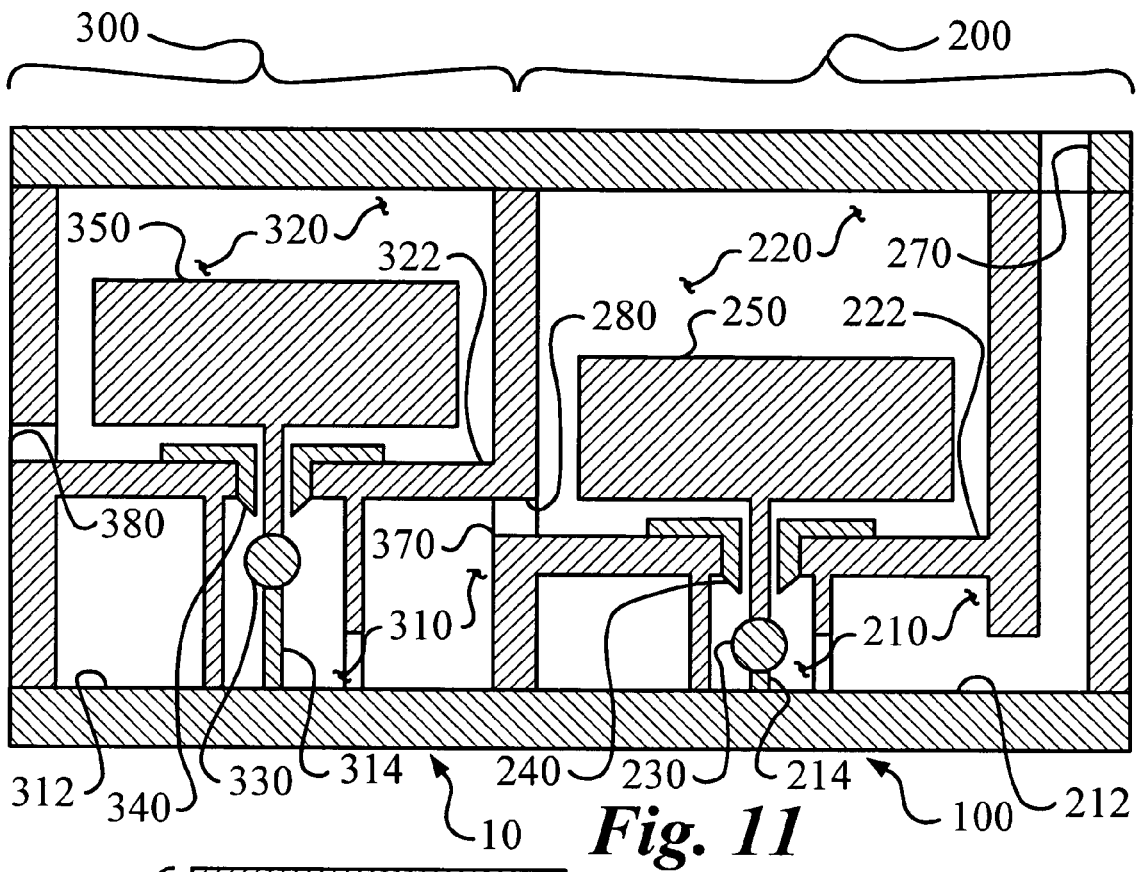
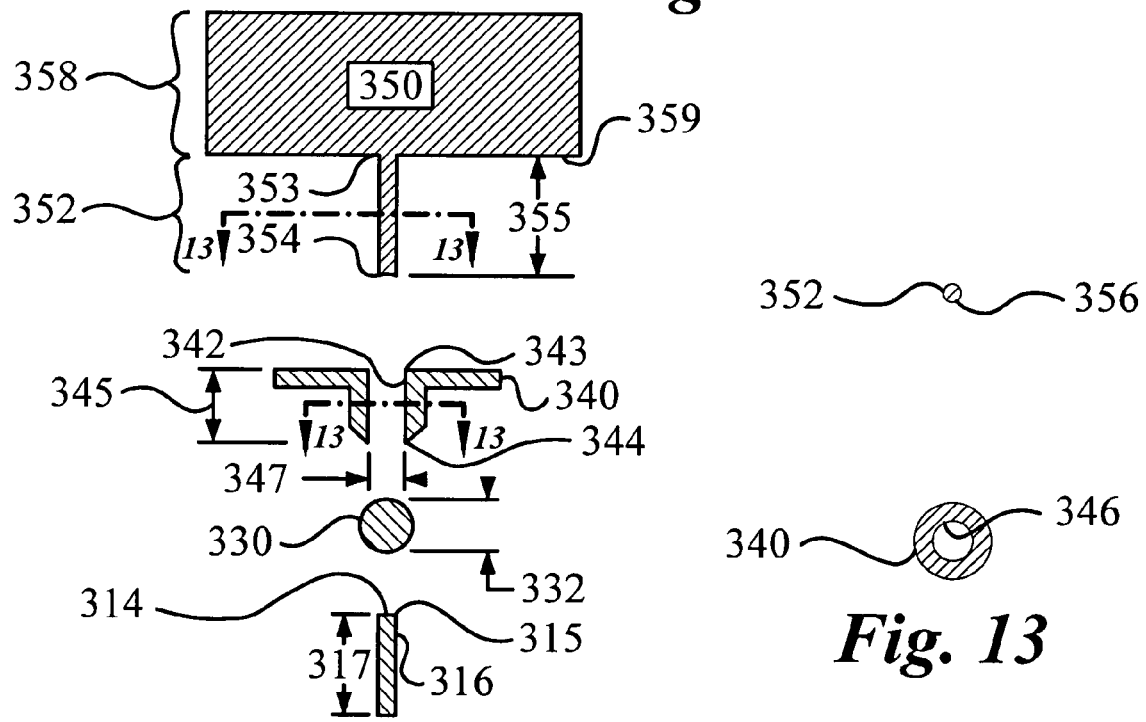
Fig. 11
Fig. 12
Fig. 13

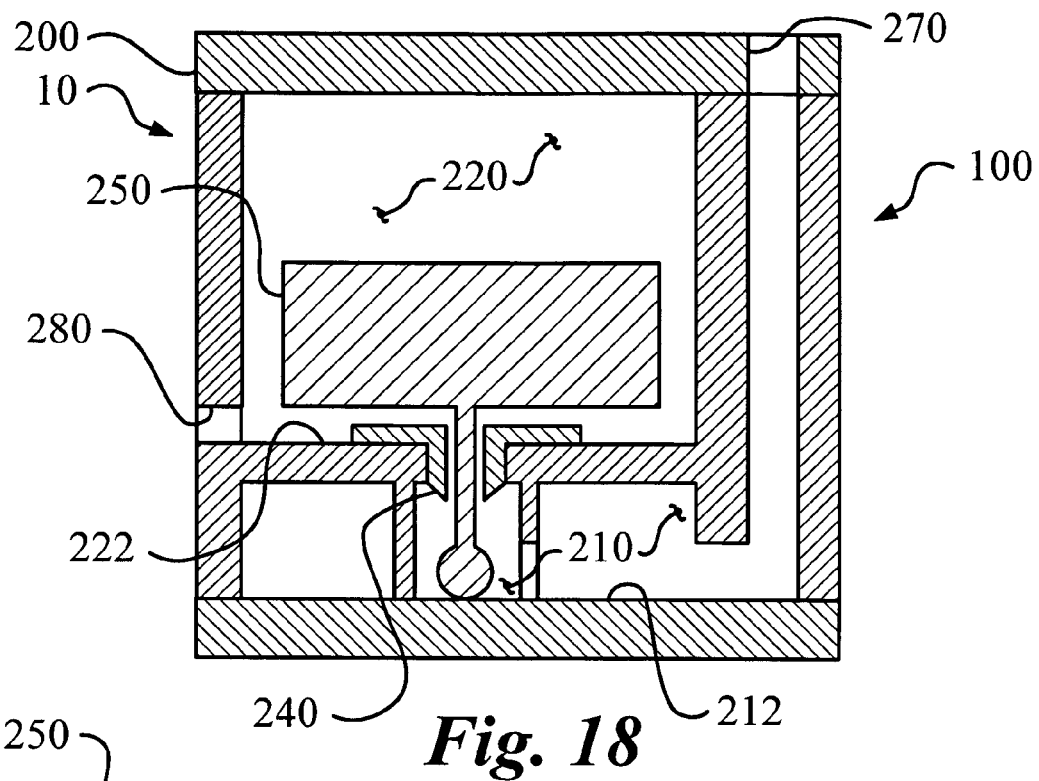
Fig. 18
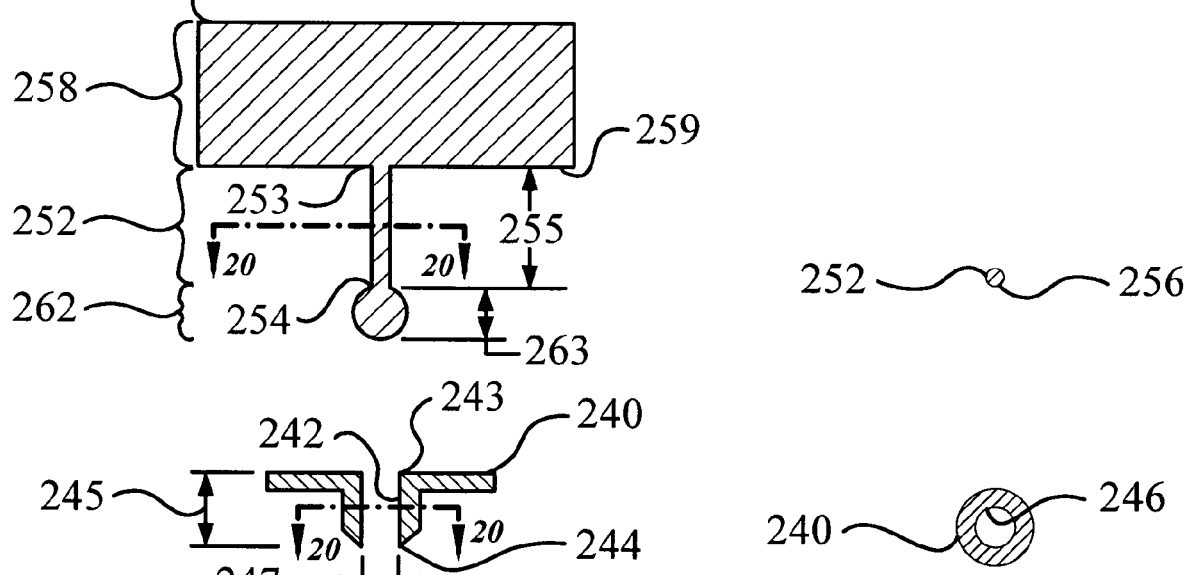
Fig. 19
Fig. 20

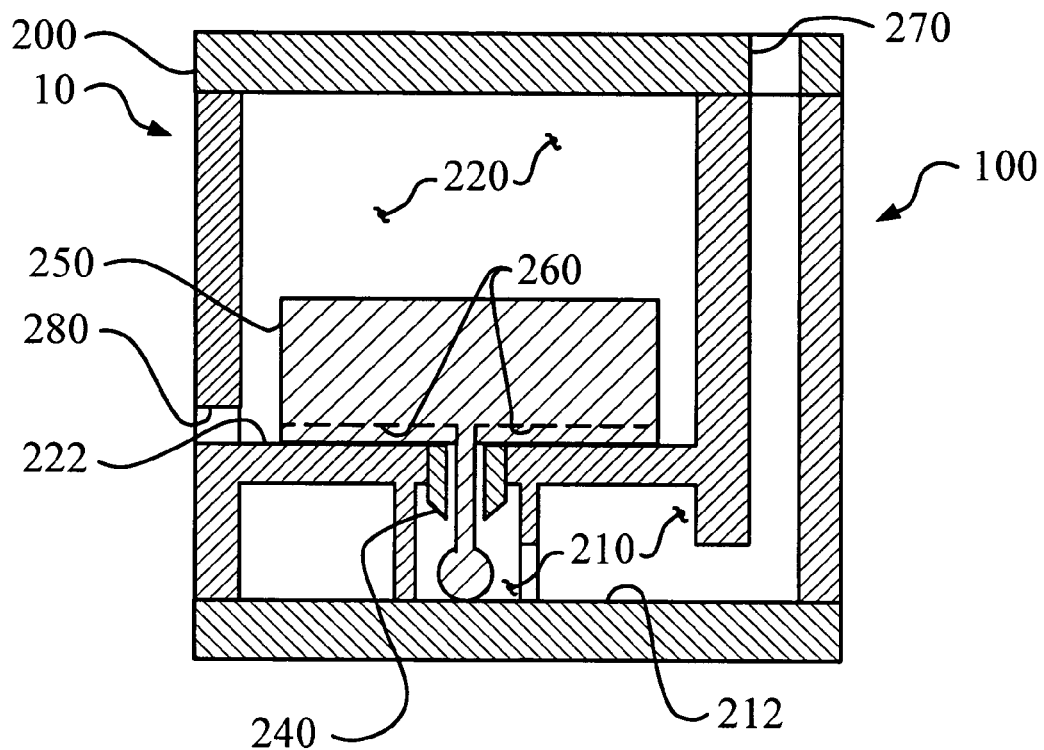
Fig. 21
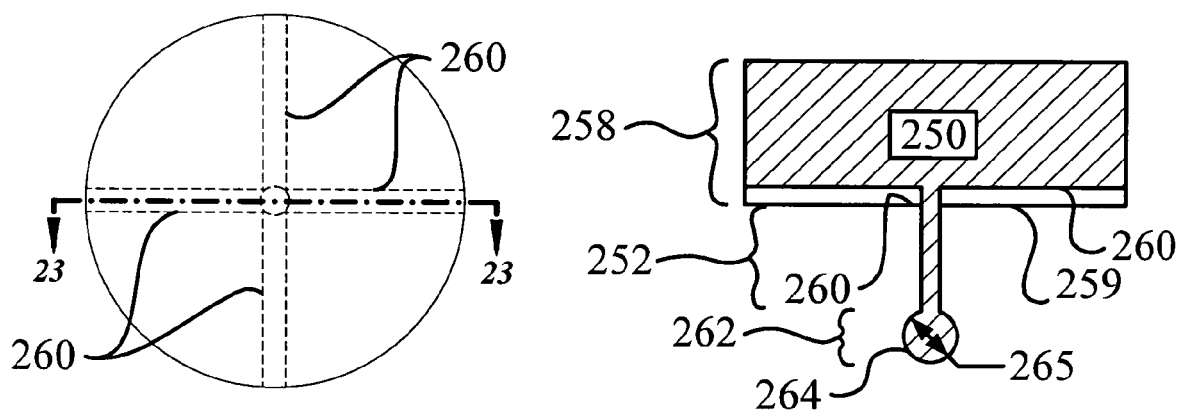
Fig. 22  Fig. 23

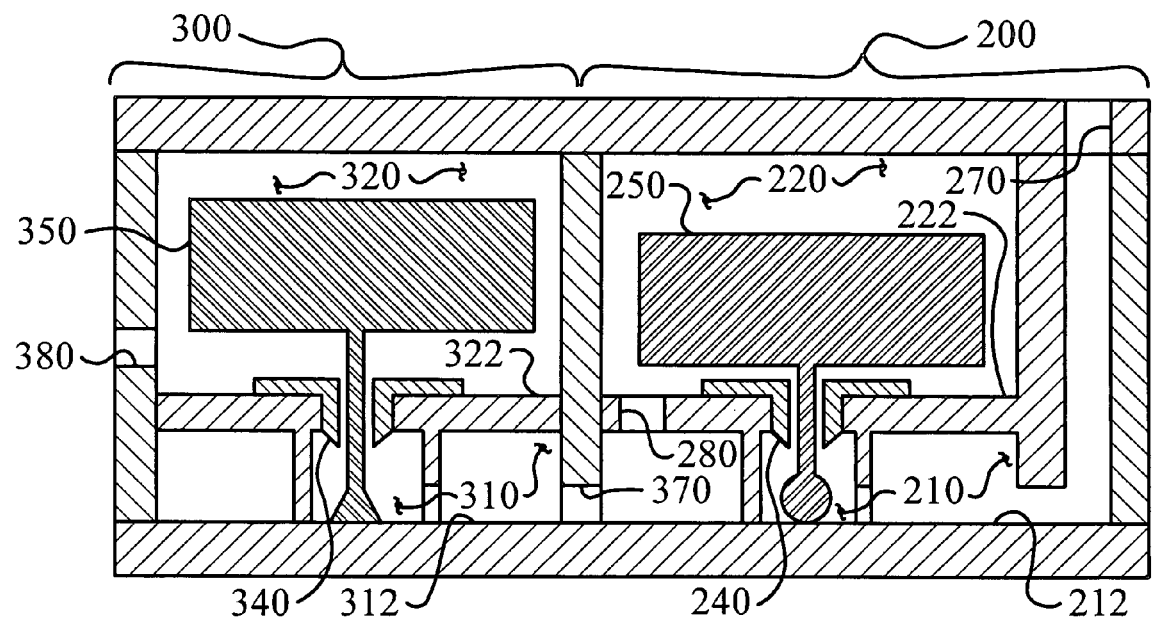
*Fig. 24*
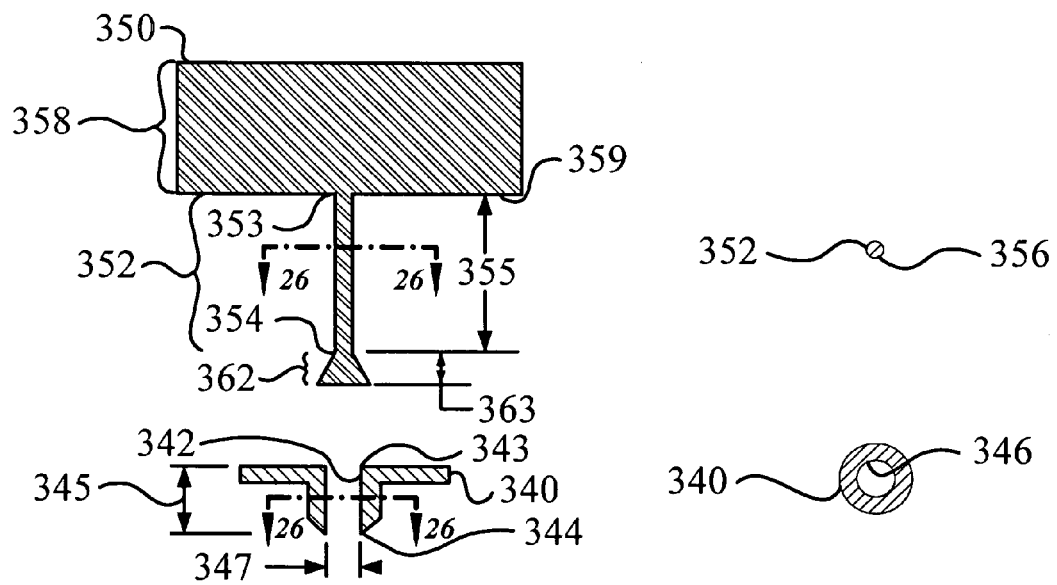
*Fig. 25*  *Fig. 26*

AUTOFEED MECHANISM FOR HEATED HUMIDIFIER CHAMBER

TECHNICAL FIELD

The present invention generally relates to an automatic flow and level control device, especially for an autofeed mechanism particularly suited for controlling the fluid level in a heated humidifier chamber.

BACKGROUND OF THE INVENTION

Automatic flow control devices have been around for hundreds, if not thousands, of years. A large portion of automatic flow control devices are dedicated to maintaining a predetermined fluid level in a reservoir, or tank. Such level maintaining automatic flow control valves have often incorporated elements that float on the surface of the fluid to indicate when the desired fluid level has been obtained. Perhaps the most famous level maintaining automatic flow control valve is that found in the storage tank of a water closet, or toilet. The water closer tank control valve includes a float mounted on a lever that is connected to a shut-off device in the water supply line. When the water in the tank rises to the desired level, the float positions the lever such that it closes the shut-off device, and accordingly the flow of water.

Such float-and-lever control devices appear relatively simple, yet as any homeowner knows, are plagued with problems. Additionally, float-and-lever control devices are not particularly well suited for miniaturization to small-scale application. Further, the level of control offered is relatively crude and not suitable for applications requiring precise level control. Still further, its reliance on an almost constantly submerged lever that must pivot in at least one location is not appropriate for critical applications. Such float-and-lever control devices are found in U.S. Pat. Nos. 3,049,144, 5,655,232, and 5,934,881.

Some automatic flow control devices have recognized the limitations imposed by the lever in the float-and-lever configuration and have incorporated an untethered float configuration. Such untethered configurations are found in U.S. Pat. Nos. 2,169,462; 2,920,644; 2,928,663; and 6,129,836. Still, many such untethered designs suffered from large size requirements and were not suitable for critical applications.

The present invention incorporates two free moving elements that cooperate across a seat connecting two distinct chambers. This configuration supports miniaturization of the automatic flow control device as well as robust operating capabilities, while capable of maintaining the fluid in a reservoir at a predetermined level with great precision.

SUMMARY OF THE INVENTION

In its most general configuration, the present invention advances the state of the art with a variety of new capabilities and overcomes many of the shortcomings of prior devices in new and novel ways. In its most general sense, the present invention overcomes the shortcomings and limitations of the prior art in any of a number of generally effective configurations. The instant invention demonstrates such capabilities and overcomes many of the shortcomings of prior methods in new and novel ways.

The instant invention includes an autofeed mechanism for controlling the flow of a fluid to a heated humidifier chamber. The autofeed mechanism includes a body defining at least a primary housing with a primary inlet chamber and a primary float chamber. A primary seat permits selective fluid communication between the primary inlet chamber and the primary float chamber. A primary float, located in the primary float chamber, and a primary ball, located in the primary inlet chamber, cooperate to either allow fluid to pass through the primary seat or block fluid from passing through the primary seat.

During operation, fluid first enters the primary fluid inlet, either under pressure or via gravity. The fluid then passes into the primary inlet chamber, where the primary ball is housed. The fluid fills the primary chamber and then enters the primary float chamber by passing through the primary seat. The fluid then travels laterally and exits the primary float chamber via the primary fluid exit. The fluid generally then fills a humidifier chamber. Here, the primary float is not influenced by the fluid and the weight of the primary float keeps the primary ball away from the primary seat. Eventually, the fluid level rises high enough that the action of the primary float on the primary ball decreases to a level that is overcome by the buoyant force of the primary ball and other fluidic forces resulting from the pressure and/or velocity of the fluid. Then, the primary ball moves away from the ball support and the elevation of the primary float increases. Finally, the primary ball rises enough to seal against the primary seat thus stopping the flow of fluid and maintaining the fluid elevation at the primary predetermined fluid level.

The invention also includes a dual housing embodiment incorporating a second autofeed system to introduce a redundancy, or fail-safe, into the autofeed mechanism. In this embodiment, the autofeed mechanism includes a body defining both a primary housing and a secondary housing. The elements of the secondary housing are substantially identical to those of the primary housing. The arrangement of the secondary housing may be identical to the primary housing with the elevation of the primary float chamber base surface equal to that of the secondary float chamber base surface; however, it is preferred to have the housings configured to alert an observer of a failure in the primary housing. Therefore, if the redundant system is required to function the fluid level produced is different than the fluid level produced if the primary system were properly functioning, therefore providing an indication of a malfunction.

These variations, modifications, alternatives, and alterations of the various preferred embodiments, arrangements, and configurations may be used alone or in combination with one another as will become more readily apparent to those with skill in the art with reference to the following detailed description of the preferred embodiments and the accompanying figures and drawings.

BRIEF DESCRIPTION OF THE DRAWINGS

Without limiting the scope of the present invention as claimed below and referring now to the drawings and figures:

FIG. 1 is a partial cross sectional view of an autofeed mechanism in accordance with the present invention, not to scale;

FIG. 2 is an exploded assembly view of several components of the autofeed mechanism of FIG. 1, not to scale;

FIG. 3 is a cross sectional view of the primary stem portion and the primary seat, taken along section lines 3-3 in FIG. 2, not to scale;

FIG. 8 is a partial cross sectional view of an embodiment of the autofeed mechanism in accordance with the present invention, not to scale;

FIG. 9 is a top plan view of the primary float, not to scale;

FIG. 10 is a cross sectional view of the primary float of FIG. 9 taken along section line 10-10, not to scale;

FIG. 11 is a partial cross sectional view of an autofeed mechanism in accordance with the present invention, not to scale;

FIG. 12 is an exploded assembly view of several components of the autofeed mechanism of FIG. 1, not to scale;

FIG. 13 is a cross sectional view of the primary stem portion and the primary seat, taken along section lines 13-13 in FIG. 12, not to scale;

DETAILED DESCRIPTION OF THE INVENTION

Figure 4:
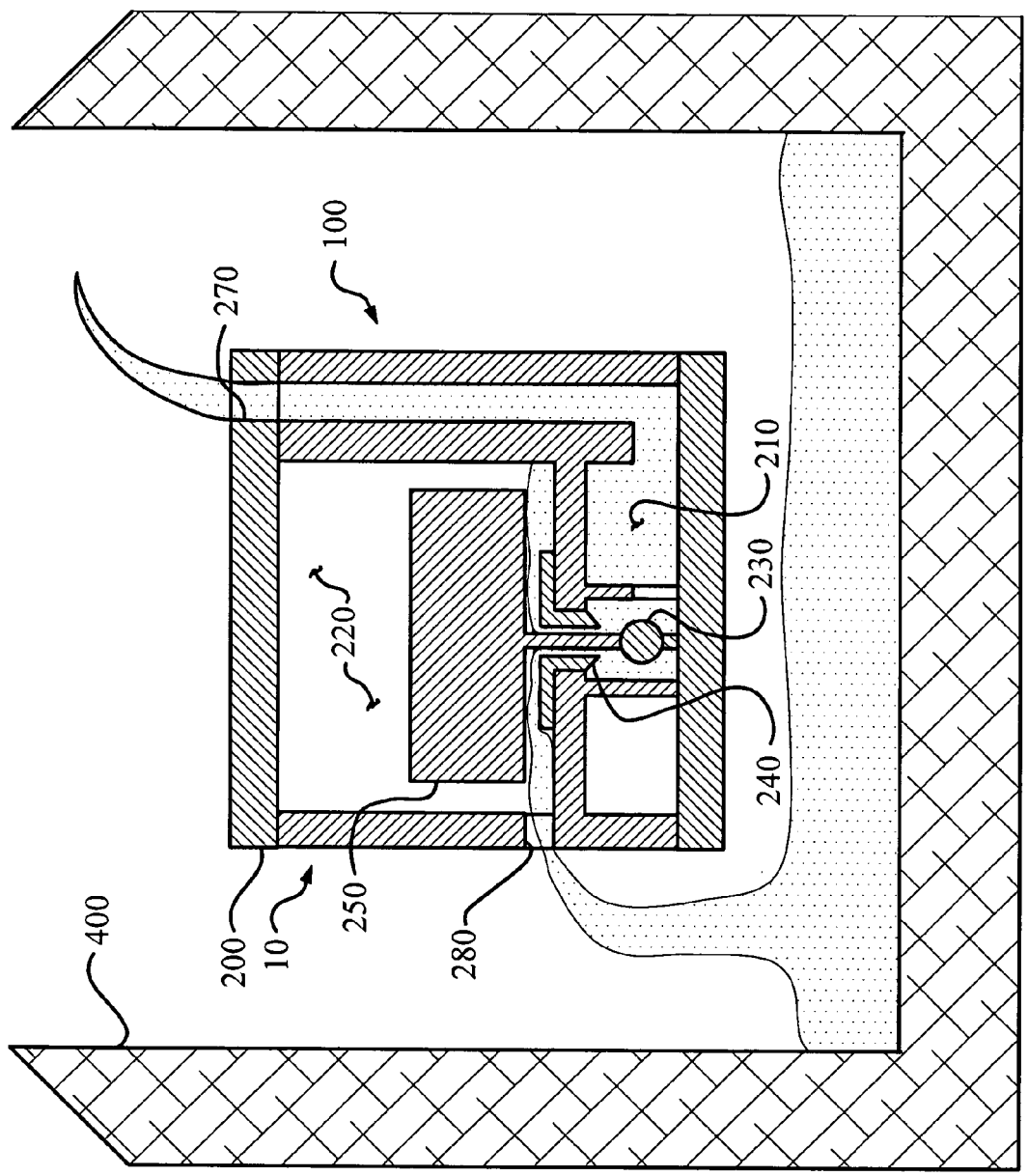
FIG. 4 is a partial cross sectional view of an embodiment of the autofeed mechanism in operation, not to scale.

The autofeed mechanism for a heated humidifier chamber (10) of the instant invention enables a significant advance in the state of the art. The preferred embodiments of the apparatus accomplish this by new and novel arrangements of elements that are configured in unique and novel ways and which demonstrate previously unavailable but preferred and desirable capabilities. The detailed description set forth below in connection with the drawings is intended merely as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention.

Referring generally to FIGS. 1 through 17, the instant invention is an autofeed mechanism (10) for controlling the flow of a fluid to a heated humidifier chamber. It should be understood that the figures are not to scale. In fact, they are highly enlarged versions of the autofeed mechanism that would be used on a heated humidifier chamber. Further, one skilled in the art will realize that the inlets and outlets will have to be sized to allow venting of air from the chamber until the balls seat. An alternative embodiment would be to place, in the primary chamber, a hydrophobic vent. These vents are well-known to those skilled in the art and a preferred hydrophobic vent is a Gore-Tex® that is found in the industry. The autofeed mechanism (10) includes a body (100) defining at least a primary housing (200) with a primary inlet chamber (210) and a primary float chamber (220), as seen in FIG. 1. A primary seat (240), in cooperation with a primary float (250) and a primary ball (230), allows selective fluid communication between the primary inlet chamber (210) and the primary float chamber (220).

The basic operation of the autofeed mechanism (10) will now be briefly described, followed by a detailed disclosure of the various components of the autofeed mechanism (10).

With continued reference to FIG. 1, the fluid first enters the primary fluid inlet (270), either under pressure or via gravity. The fluid then passes into the primary inlet chamber (210), where the primary ball (230) is housed. The fluid fills the primary chamber (210) and then enters the primary float chamber (220) by passing through the primary seat (240), which is partially blocked by a portion of the primary float (250). The fluid then travels laterally and exits the primary float chamber (220) via the primary fluid exit (280). The fluid generally then fills a humidifier chamber (400). This first filling of the autofeed mechanism (10) is illustrated in FIG. 4.

A few aspects of the structure of the autofeed mechanism (10) warrant review before proceeding with the sequence of operation of the mechanism (10). First, with respect to the primary inlet chamber (210), it has an inlet chamber base surface (212), seen best in FIG. 1 that may be thought of as the floor, or bottom, of the primary inlet chamber (210).

Second, with respect to the primary seat (240), best illustrated in exploded view FIG. 2, it has a primary seat channel (242) with a distal end (243) open to the primary float chamber (220) and a proximal end (244) open to the primary inlet chamber (210). The distance from the distal end (243) to the proximal end (244) defines a primary channel length (245). Additionally, the primary seat channel (242) has an opening cross sectional area (246), illustrated in FIG. 3 representing a cross sectional view of the primary seat channel (242) taken along section line 3-3 of FIG. 2.

Third, with respect to the primary float (250), it has a float portion (258), identified in FIG. 2, located in the primary float chamber (220), and a stem portion (252), also identified in FIG. 2, projecting toward the primary seat (240) and substantially parallel with the primary seat channel (242). The primary float chamber (220) is configured to allow the primary float (250) to move within the chamber (220) when acted upon by the fluid and/or the primary ball (230). Further, the stem portion (252) cooperates with the primary seat (240) so that it may move within the primary seat channel (242) with the movement of the primary float (250). The stem portion (252) has a distal end (253) at the connection to the float portion (258) and a proximal end (254) nearest the primary seat (240) with the distance between the distal end (253) and the proximal end (254) defining a stem length (255). The stem portion (252) has a stem cross sectional area (256) less than the primary seat channel opening cross sectional area (246) thereby permitting the fluid to flow through primary seat channel (242) when the stem portion (252) is in the primary seat channel (242).

Figure 6:
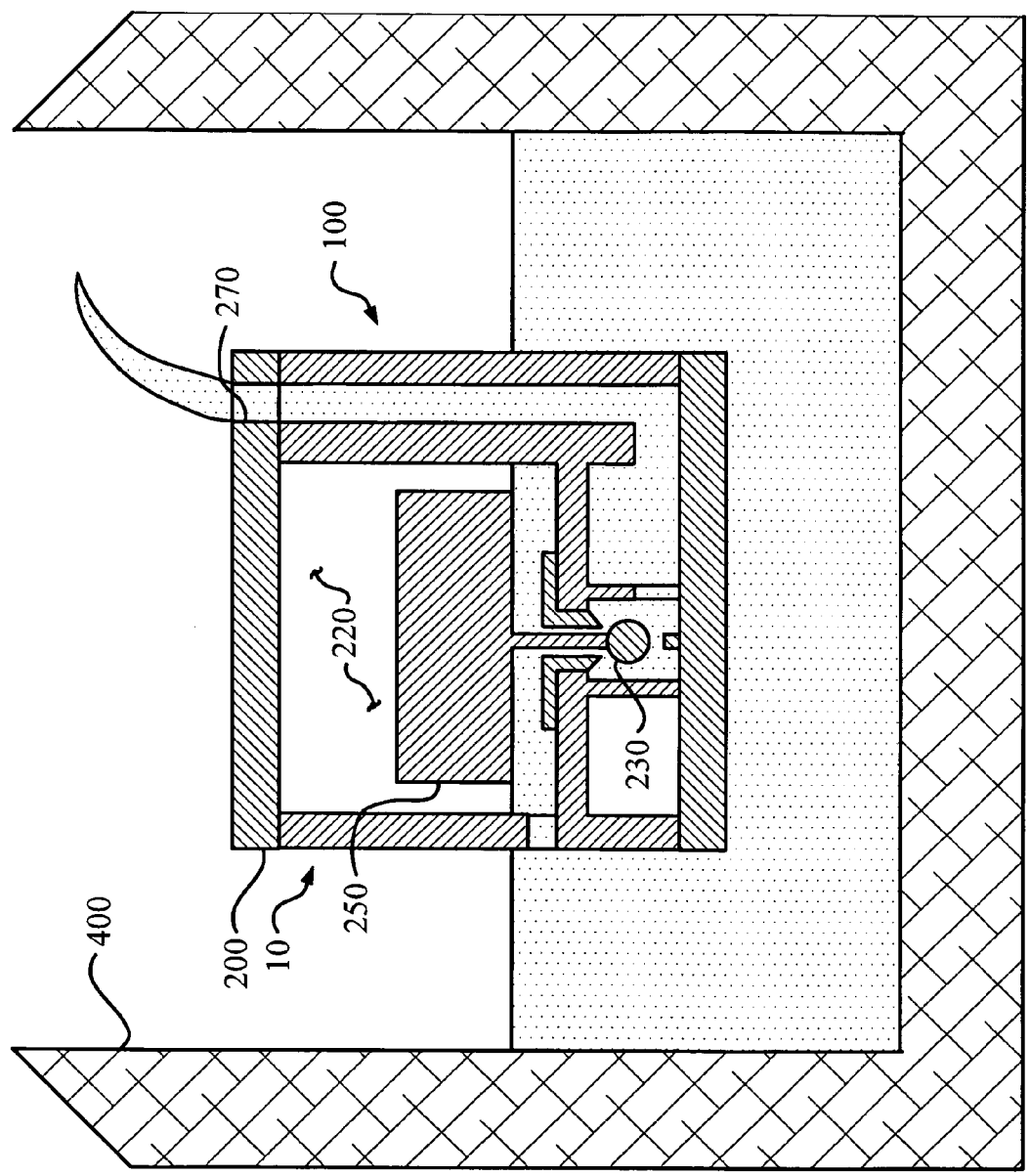
FIG. 6 is a partial cross sectional view of an embodiment of the autofeed mechanism in operation, not to scale.
Figure 7:
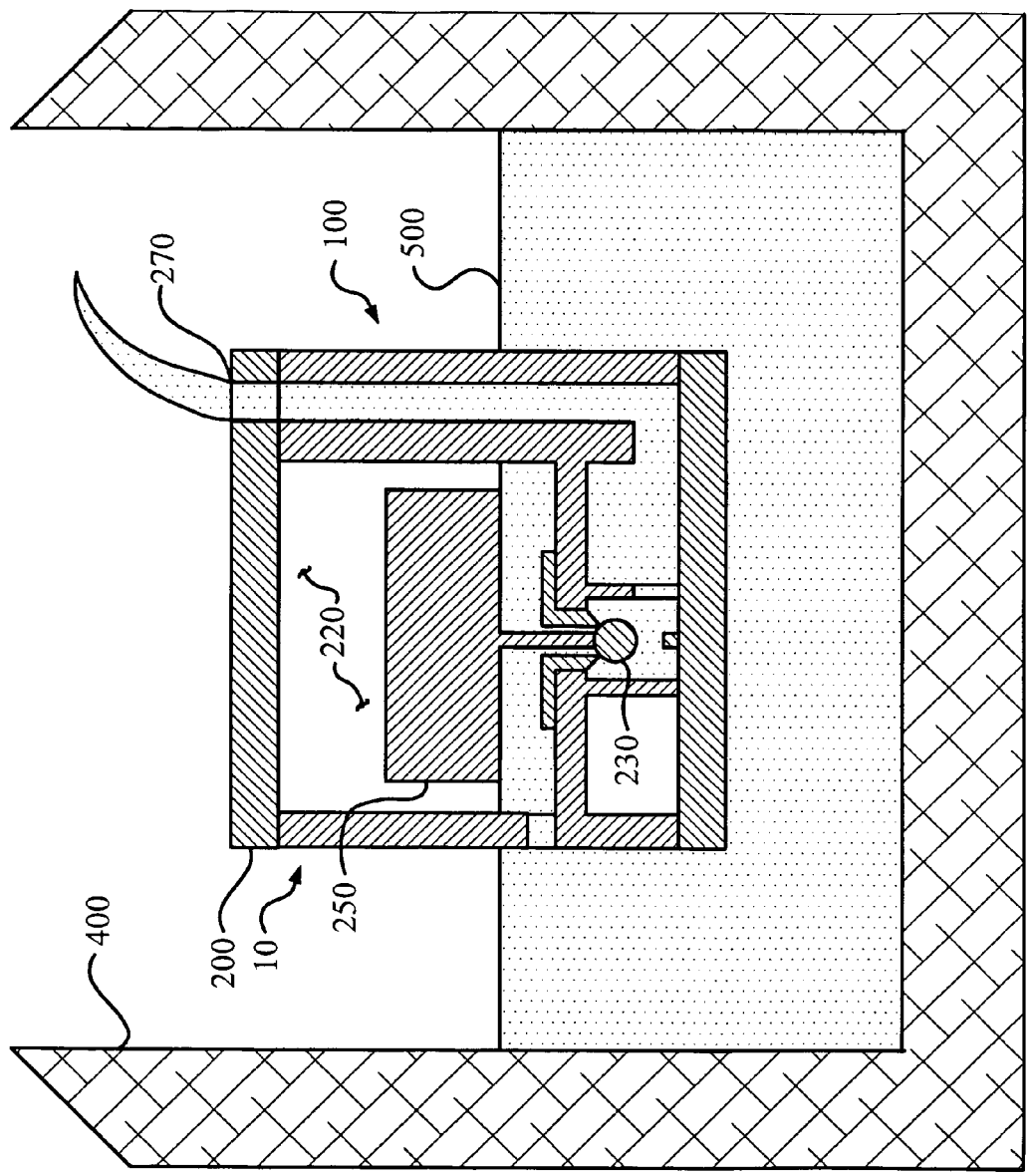
FIG. 7 is a partial cross sectional view of an embodiment of the autofeed mechanism in operation, not to scale.

Fourth, with respect to the primary ball (230), it has a diameter (232) and is located in the primary inlet chamber (210) such that the center of the primary ball (230) is substantially collinear with a central axis of the primary float stem portion (252). As previously mentioned, the primary ball (230) is acted upon by the primary float stem portion (252) thereby forcing the primary ball (230) against a ball support (214), until a predetermined fluid level is reached that begins to float the primary float (250) thereby reducing its action on the primary ball (230) and allowing the primary ball (230) to float away from the ball support (214), or the buoyant force of the primary ball (230) and the fluidic forces overtake the action of the primary float (250) causing it to move away from the primary seat (240), as seen in FIG. 6. The ball support (214) is a projection extending from the inlet chamber base surface (212) a support length (217) distance thus allowing fluid entering the primary inlet chamber (210) to pass the primary ball (230) and exit to the primary float chamber (220) and the primary fluid exit (280) by passing through the primary seat (240) around the stem portion (252). Eventually the fluid level reaches a predetermined primary fluid elevation (500) at which the action of the primary float (250) on the primary ball (230) has been reduced to the point that the primary ball (230) floats away from the ball support (214) and seals the primary seat channel proximal end (244), thereby preventing the fluid from flowing from the primary inlet chamber (210) to the primary float chamber (220) thus stopping the flow of fluid., as seen in FIG. 7.

Now, referring again to the sequence of operation, FIG. 4 illustrates the initial filling of the primary inlet chamber (210) whereby the primary float (250) is not influenced by the fluid and the weight of the primary float (250) keeps the primary ball (230) against the ball support (214) and away from the primary seat (240). As one with skill in the art will recognize, to keep the primary ball (230) against the ball support (214) the weight of the primary ball (230) must overcome the buoyant force developed due to the total submersion of the primary ball (230) and any fluidic forces.

Figure 5:
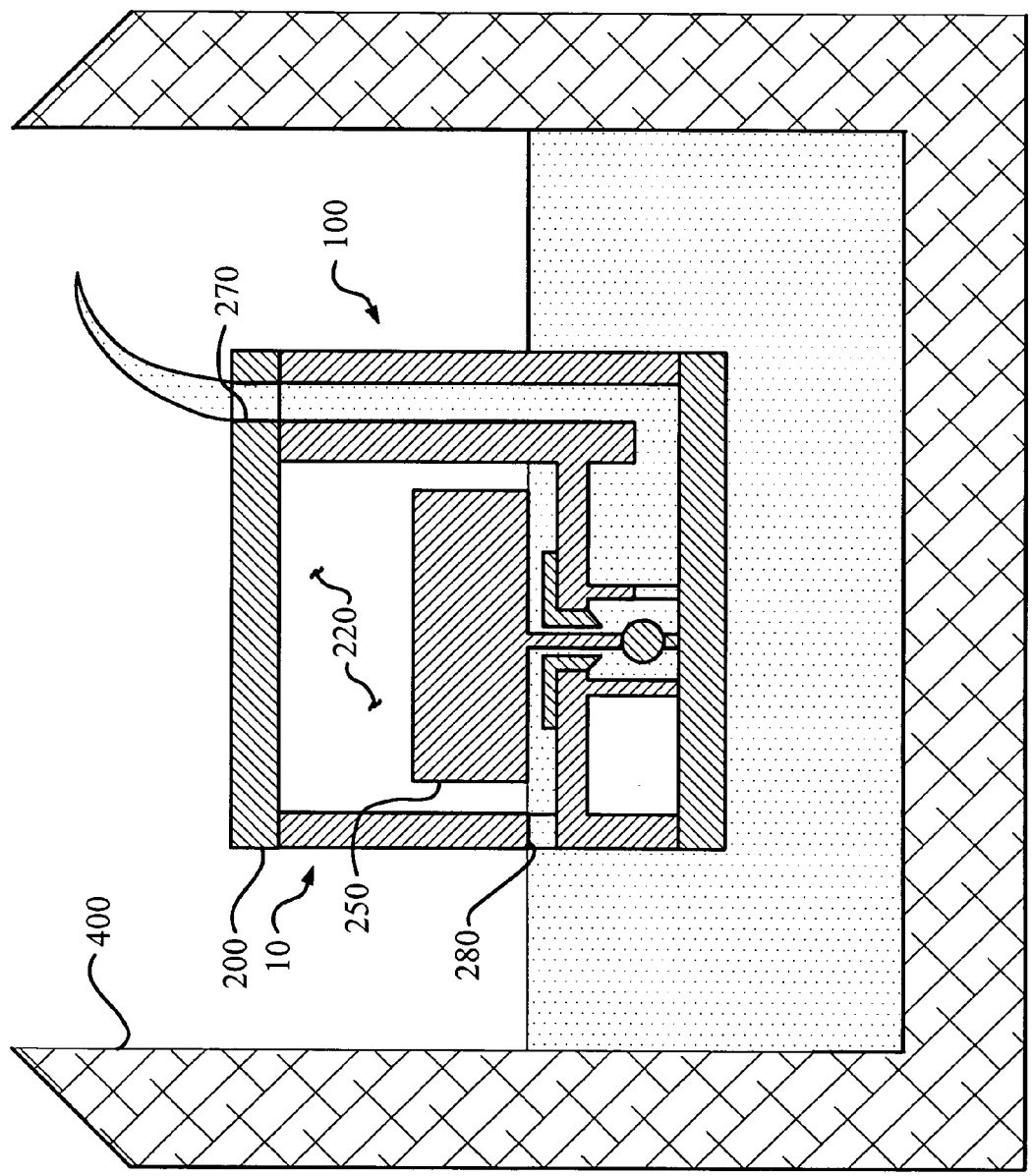
FIG. 5 is a partial cross sectional view of an embodiment of the autofeed mechanism in operation, not to scale.

Next, FIG. 5 illustrates a subsequent situation in which the fluid has now filled the primary inlet chamber (210) and the humidifier chamber (400) and the primary float chamber (220) up to the normal elevation of the float portion base surface (259), labeled in FIG. 2. Whether or not the primary float (250) begins to float at this fluid elevation depends on the construction of the primary float (250). A hollow primary float (250), or one of low density, may float at this elevation, whereas a solid primary float (250), or one of high density, may require a higher fluid elevation to begin to float. However, it is important to note that the operation of the present invention is not dependent upon the actual floating of the primary float (250), but rather a reduction in action on the primary ball (230) such that it may cooperate with the primary seat (240) to stop the flow of fluid. Thus, the primary float (250) functions as a counterbalance and need only counter the primary ball (230) buoyant force and any present fluidic forces. Further, the density of the primary float (250) and the primary ball (230), as well as the size and geometry of the primary float (250) and primary ball (230), may be changed to accommodate the range of elevations and pressures anticipated.

FIG. 6 illustrates the next level in which the primary ball (230) has moved away from the ball support (214) and the elevation of the primary float (250) has increased. Finally, FIG. 7 illustrates the primary ball (230) seated against the primary seat (240) thus stopping the flow of fluid and maintaining the fluid elevation at the primary predetermined fluid level (500).

Referring again to FIGS. 1 and 2, in one particular embodiment the orthogonal distance from the inlet chamber base surface (212) to the primary seat channel distal end (243) is less than the total of the support length (217), the primary ball diameter (232), and the stem length (255). This embodiment ensures the presence of a gap between the primary seat channel proximal end (244) and a float portion base surface (259) to ensure that the float portion base surface (259) does not block the primary seat channel (242) and to facilitate the flow of fluid into the primary float chamber (220). In an alternative embodiment seen in FIGS. 8, 9, and 10, the orthogonal distance from the inlet chamber base surface (212) to the primary seat channel distal end (243) is substantially equal to the total of the support length (217), the primary ball diameter (232), and the stem length (255), and a float portion base surface (259) is formed with at least one flow channel (260) to facilitate the flow of fluid from the primary seat channel (242) into the primary float chamber (220). In this embodiment, the primary float portion base surface (259) may rest directly on the primary seat (240) and not impede the fluid flow because the fluid exits the primary seat channel (242) into at least one flow channel (260) and directs the fluid to the primary float chamber (220).

Referring again to FIGS. 1 and 2, the cooperation between the primary float (250), the primary seat (240), the primary ball (230), and the ball support (214) is essential. As previously disclosed, the center of the primary ball (230) is substantially collinear with a central axis of the primary float stem portion (252). In a further embodiment, the ball support (214) is substantially collinear with the center of the primary ball (230) and with a central axis of the stem portion (252). While the ball support (214) is generally described as projecting from the primary inlet chamber base surface (212), one with skill in the art will recognize that it may equally be a recess formed in the primary inlet chamber base surface (212), or merely a tightly confined area to control the motion of the primary ball (230).

The primary float stem portion (252) is designed to be releasably received by the primary seat channel (242), yet permit the flow of fluid between the stem portion (252) and the seat channel (242). Therefore, the stem cross sectional area (256) must be less than the primary seat channel opening cross sectional area (246), as seen in FIG. 3. In one particular embodiment, the stem cross sectional area (256) is at least ten percent less than the primary seat channel opening cross sectional area (246).

Further, the primary seat channel distal end (244) must be configured to cooperate with the primary ball (230) to ensure that the primary ball (230) creates a liquid-tight seal against the primary seat (240). As such, in one particular embodiment the primary seat channel opening cross sectional area (246) at the primary seat channel proximal end (244) is at least ten percent less than the maximum cross sectional area of the primary ball (230). One with skill in the art will appreciate that despite the use of the word "ball," the primary ball (230) need not be spherical in shape, in fact, it may be any object that will create a seal against the primary seat (240) and can be displaced by the primary float (250). In fact, the primary ball (230) may be virtually any geometric shape, including, but not limited to, a conical shape or a flat shape such as a film or disk.

Now, with the embodiments of FIGS. 1-10 disclosed, a dual housing embodiment will be disclosed. Referring generally to FIGS. 11 through 17, the instant embodiment incorporates a second autofeed system to introduce a redundancy, or fail-safe, into the autofeed mechanism (10) of the present invention. In this embodiment the autofeed mechanism (10) includes a body (100) defining a primary housing (200) and a secondary housing (300). The elements of the secondary housing (300) are substantially identical to those of the primary housing (200), only now with reference numerals in the 300's rather than the 200's, and incorporating reference to "secondary" in the element description, rather than the references to "primary" associated with the elements of the primary housing (200). Therefore, the prior disclosure with respect to the primary housing (200) will not be repeated here, it is incorporated by reference with respect to FIGS. 11, 12, and 13, in lieu of FIGS. 1, 2, and 3, and the secondary housing (300) elements.

The setup of the secondary housing (300) may be identical to the primary housing (200) with the elevation of the primary float chamber base surface (222) equal to that of the secondary float chamber base surface (322), however it is preferred to have the housings (200, 300) setup to alert an observer of a failure in the primary housing (200). Therefore, as seen in FIGS. 11 and 12, the secondary float chamber base surface (322) is higher in elevation than the primary float chamber base surface (222) and the secondary ball support length (317) is greater than the primary ball support length (217) thus establishing a secondary fluid level (600) that is higher in elevation than the primary fluid level (500), thereby providing a visual indication that the components of the primary housing (200) are not properly functioning. In this embodiment, the primary fluid exit (280) is in fluid communication with the secondary fluid inlet (370). A failed primary float can be indicated by an elevated water level that is established by raising the base of the secondary float chamber. The elevated water level can also be established by changing the configuration of the secondary float. This will change the affect on the buoyancy and therefore delay the elevation of the secondary float leading to higher water level in the chamber. Since the design of this autofeed places a ball in the direct flow path upstream to the seat, the design is resistant to leakage due to elevated water levels in the feed bag. In other words, in the typical design the higher the water bag, the more water pressure on the seat and the greater the chance of dislodging the mechanism that seals the seat. With this design, the higher water pressure actually does the opposite and forces the ball further onto the seat. This will result in the humidifier chamber not getting water, but it will also ensure that the patient does not get drowned by the water in the bag.

Figure 14:
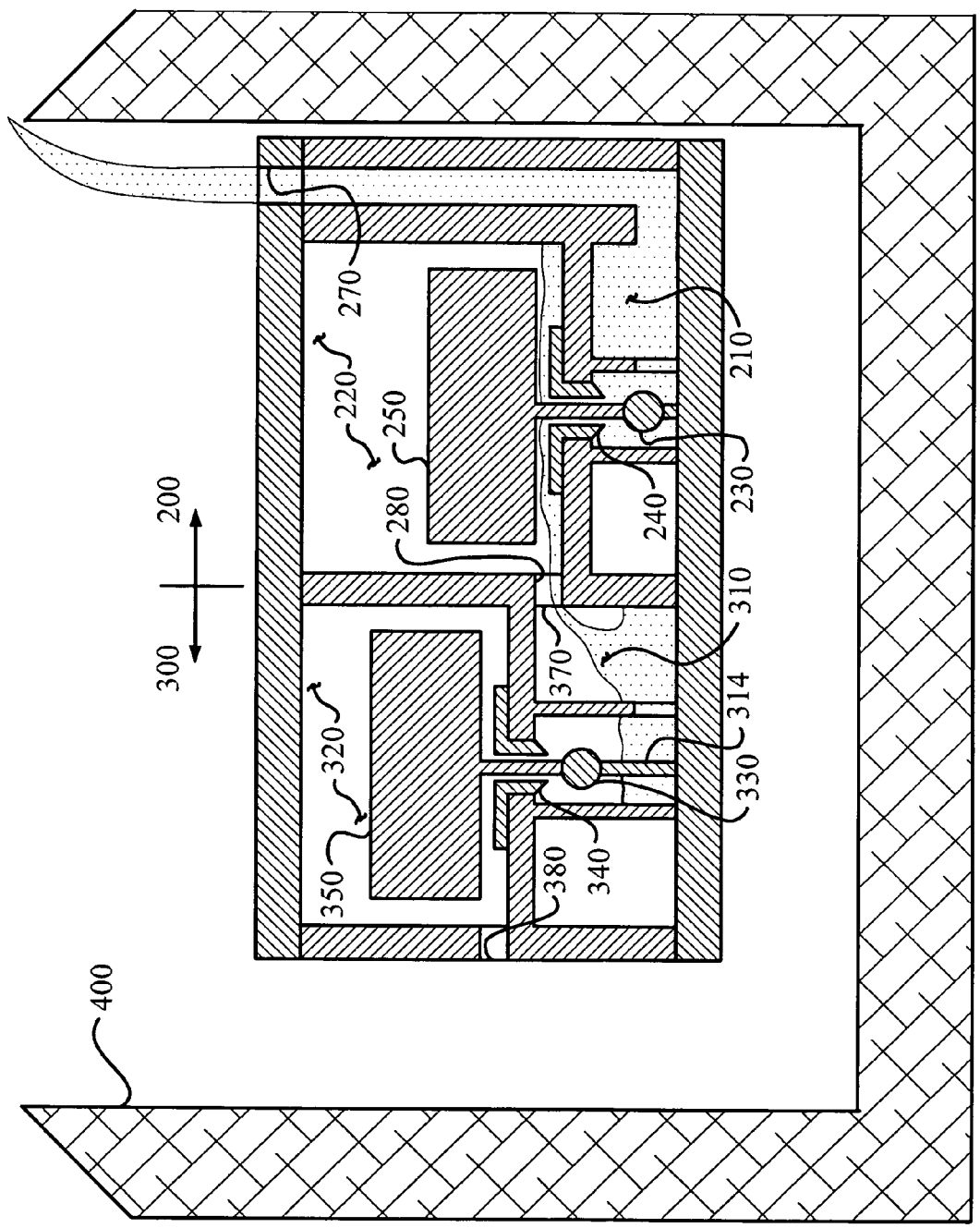
FIG. 14 is a partial cross sectional view of an embodiment of the autofeed mechanism in operation, not to scale.

Now, referring to the sequence of operation, FIG. 14 illustrates the initial filling of the primary inlet chamber (210) and the secondary inlet chamber (310) whereby the primary float (250) and the secondary float (350) are not influenced by the fluid and the weight of the primary float (250) keeps the primary ball (230) against the primary ball support (214) and away from the primary seat (240) and the weight of the secondary float (350) keeps the secondary ball (330) against the secondary ball support (314) and away from the secondary seat (340). As one with skill in the art will recognize, to keep the primary ball (230) against the ball support (214) the weight of the primary ball (230) must overcome the buoyant force developed due to the total submersion of the primary ball (230) and any fluidic forces.

Figure 15:
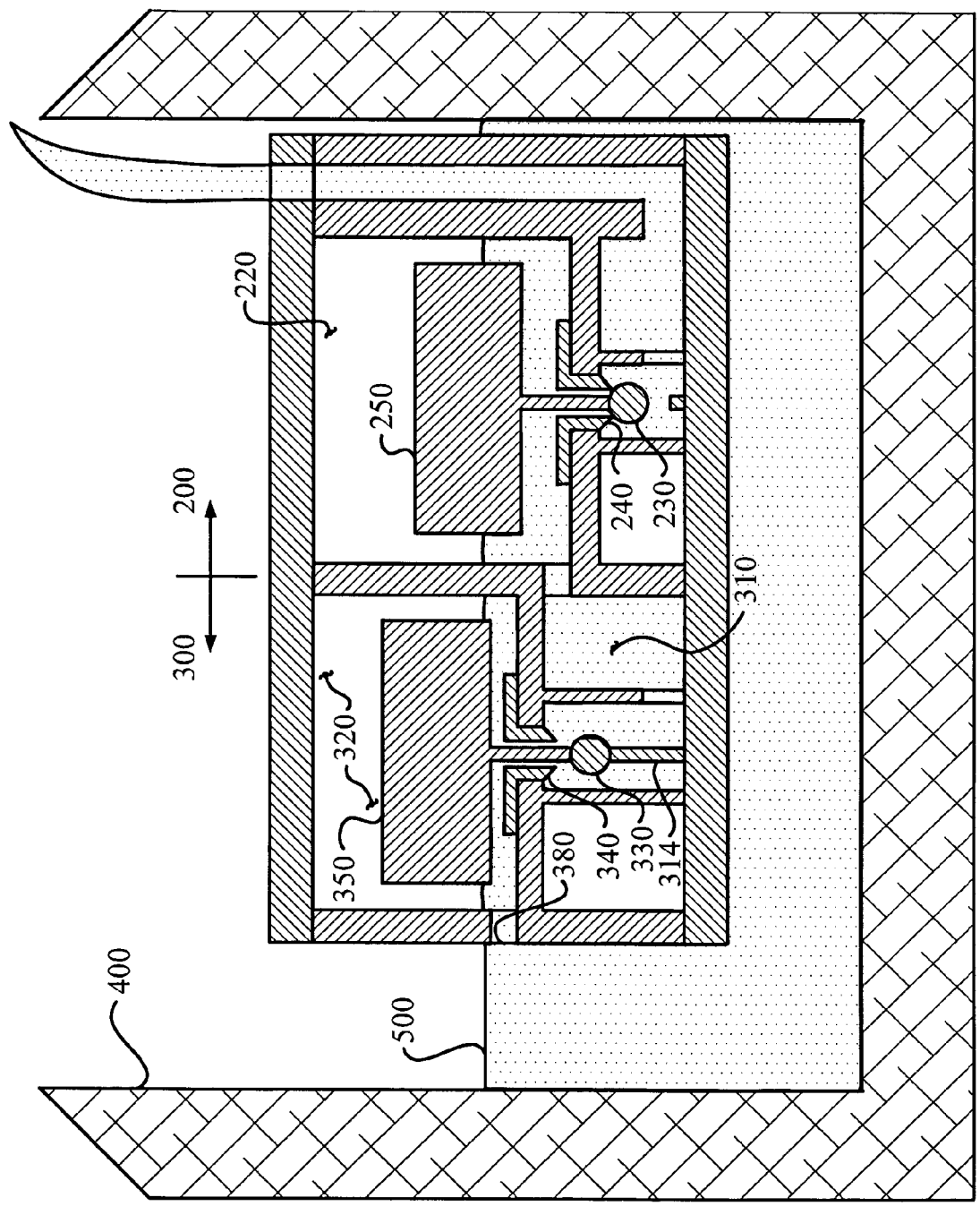
FIG. 15 is a partial cross sectional view of an embodiment of the autofeed mechanism in operation, not to scale.

Next, FIG. 15 illustrates the situation in which the components of the primary housing (200) function properly and the primary ball (230) stops the flow of fluid through the primary seat (240), thus maintaining the primary fluid level (500). In this situation, the fluid level has not increased enough to reduce the action of the secondary float (350) on the secondary ball (330) to the point that the secondary ball (330) leaves the secondary ball support (314).

Figure 16:
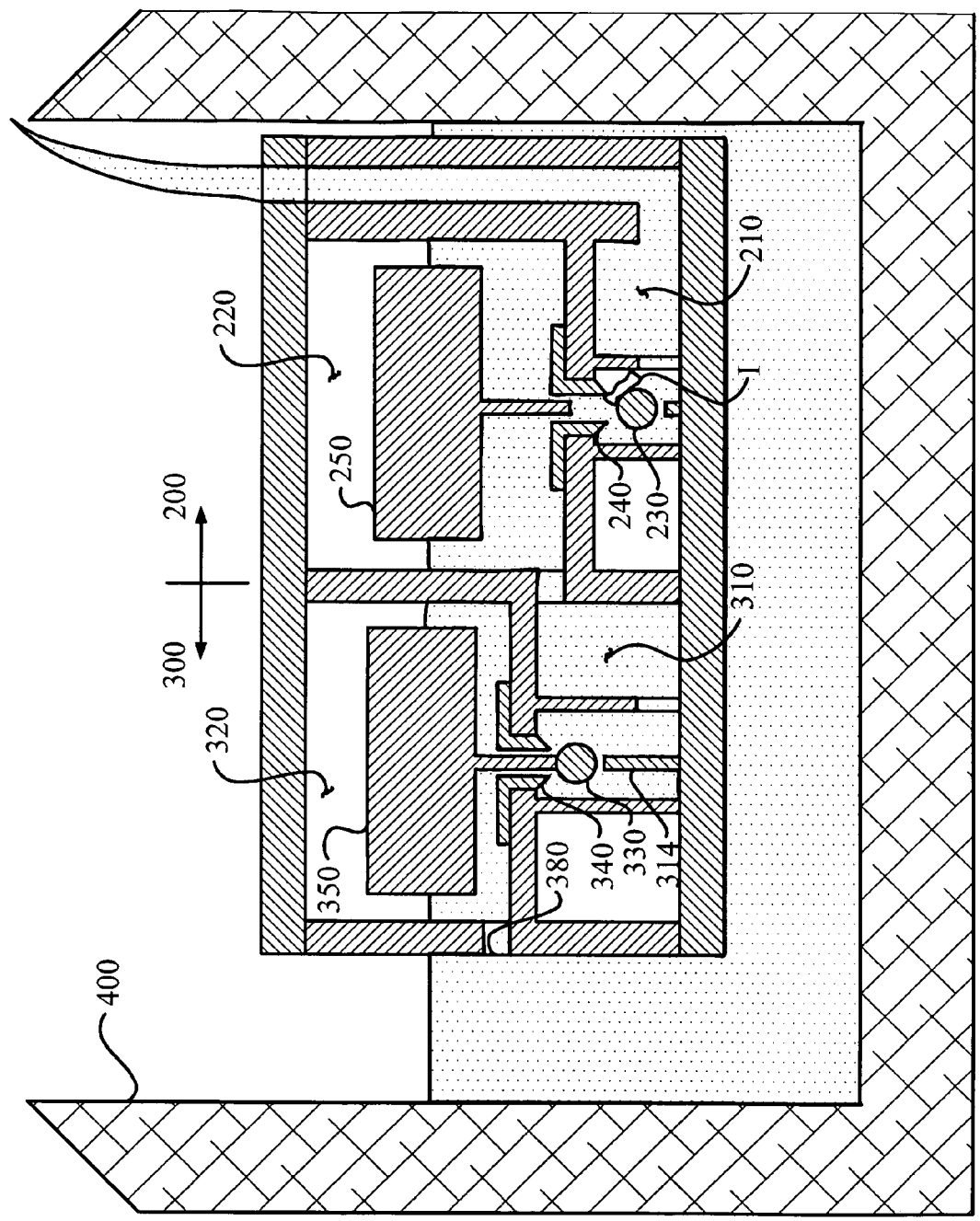
FIG. 16 is a partial cross sectional view of an embodiment of the autofeed mechanism in operation, not to scale.
Figure 17:
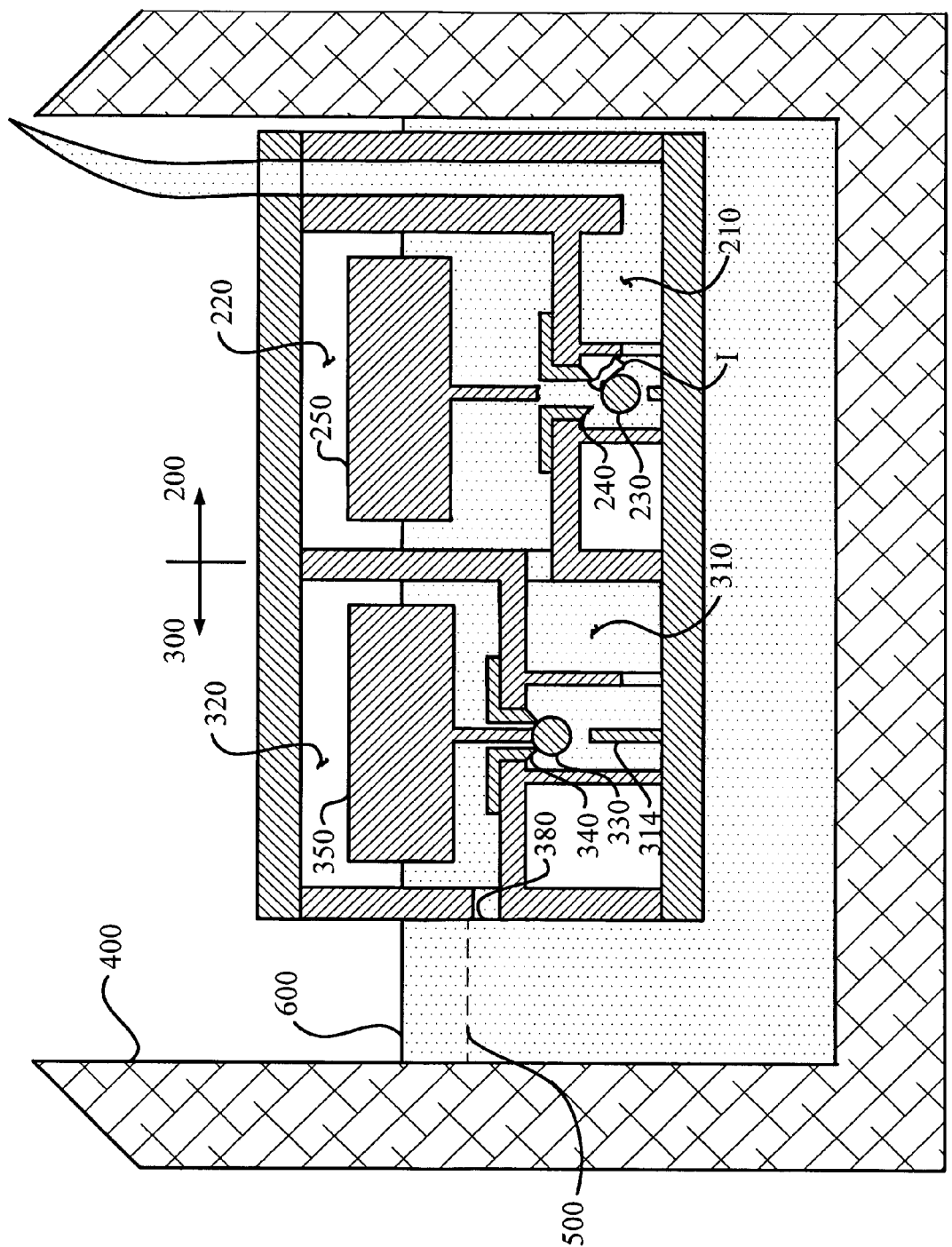
FIG. 17 is a partial cross sectional view of an embodiment of the autofeed mechanism in operation, not to scale.

FIG. 16 illustrates a situation in which an impediment (I) is lodged between the primary ball (230) and the primary seat (240), thus preventing the primary ball (230) from sealing against the primary seat (240). In such a situation, the fluid level would continue to rise in an uncontrolled manner if not for the presence of the secondary housing (300). Here, the fluid level rises until the force exerted on the secondary ball (330) by the secondary float (350) is reduced to the point that it is overcome by the buoyant force of the secondary ball (330) resulting in the secondary ball (330) leaving the secondary ball support (314), as seen in FIG. 16. Eventually the secondary ball (330) closes the secondary seat channel proximal end (344) once the fluid level has reached the secondary fluid level (600). The difference in elevation between the secondary fluid level (600) and the primary fluid level (500), seen in FIG. 17, provides an indication to the operator that the autofeed mechanism (10) is not properly functioning and requires service. Any number of audio, visual, and tactile alarm indicators may be incorporated into the autofeed mechanism (10) to sense the change in normal fluid level and warn of malfunctions.

One with skill in the art will recognize that the humidifier chamber (400) illustrated in the accompanying figures is merely schematic in nature. Further, the autofeed mechanism (10) and its components may be fabricated from a wide variety of materials, selected to reflect particular characteristic desired for operation with a variety of fluids, including, by way of example and not limitation, metals, plastic, glass, natural and synthetic rubbers, and composites of various types.

Numerous alterations, modifications, and variations of the preferred embodiments disclosed herein will be apparent to those skilled in the art and they are all anticipated and contemplated to be within the spirit and scope of the instant invention. For example, although specific embodiments have been described in detail, those with skill in the art will understand that the preceding embodiments and variations can be modified to incorporate various types of substitute and or additional or alternative materials, relative arrangement of elements, and dimensional configurations. Accordingly, even though only few variations of the present invention are described herein, it is to be understood that the practice of such additional modifications and variations and the equivalents thereof, are within the spirit and scope of the invention as defined in the following claims.

INDUSTRIAL APPLICABILITY

The autofeed mechanism for a heated humidifier chamber answers a long felt need for a novel flow control device that eliminates the problems commonly associated with lever actuated flow control systems. The mechanism is easy to manufacture and assemble due, in part, to the low number of moving components. The simple construction results in a significant advance over prior art autofeed devices. Further, the various components of the present invention are easily changed out to adjust the operating parameters of the mechanism, a feature lacking from the prior art.

We claim:

1. An autofeed mechanism for a heated humidifier chamber (10) for controlling the flow of a fluid, comprising:
a body (100) defining a primary housing (200), having a primary inlet chamber (210) with an inlet chamber base surface (212), and a primary float chamber (220), wherein the primary inlet chamber (210) has a primary fluid inlet (270), through which the fluid enters the primary inlet chamber (210), and the primary float chamber (220) has a primary fluid exit (280), through which the fluid exits the primary float chamber (220);
a primary seat (240) facilitating fluid communication between the primary inlet chamber (210) and the primary float chamber (220) having a primary seat channel (242) with a distal end (243) open to the primary float chamber (220), a proximal end (244) open to the primary inlet chamber (210), wherein the distance from the distal end (243) to the proximal end (244) defines a primary channel length (245), and an opening cross sectional area (246);
a primary float (250) having a float portion (258), located in the primary float chamber (220), and a stem portion (252) projecting toward the primary seat (240) and substantially parallel with the primary seat channel (242), wherein the primary float chamber (220) is configured to allow the primary float (250) to move freely in the primary float chamber (220) when acted upon, and wherein the stem portion (252) cooperates with the primary seat (240) 50 that it may move within the primary seat channel (242) with the movement of the primary float (250), and the stem portion (252) has a distal end (253) at the connection to the float portion (258) and a proximal end (254) nearest the primary seat (240) with the distance between the distal end (253) and the proximal end (254) defining a stem length (255), and the stem portion (252) has a stem cross sectional area (256) less than the primary seat channel opening cross sectional area (246) thereby permitting the fluid to flow through primary seat channel (242) when the stem portion (252) is in the primary seat channel (242);

a primary ball (230), having a diameter (232), located in the primary inlet chamber (210) and configured such that the center of the primary ball (230) is substantially collinear with a central axis of the stem portion (252), and the primary ball (230) is acted upon by the primary float stem portion (252) thereby forcing the primary ball (230) against a support surface associated with the inlet chamber base surface (212) thus allowing fluid entering the primary inlet chamber (210) to pass the primary ball (230) and exit to the primary float chamber (220) and the primary fluid exit (280) by passing through the primary seat (240) around the stem portion (252), until the fluid level reaches a predetermined primary fluid elevation (500) thereby reducing the action of the stem portion (252) on the primary ball (230) and allowing the primary ball (230) to float away from the support surface and seal the primary seat channel proximal end (244) thereby preventing the fluid from flowing from the primary inlet chamber (210) to the primary float chamber (220) thus stopping the flow of fluid.

2. The autofeed mechanism (10) of claim 1, further including a ball support extending from the inlet chamber base surface to form the support surface at a support length distance, and wherein the orthogonal distance from the inlet chamber base surface (212) to the primary seat channel distal end (243) is less than the total of the support length (217), the primary ball diameter (232), and the stem length (255) thereby ensuring the presence of a gap between the primary seat channel proximal end (244) and a float portion base surface (259) to facilitate the flow of fluid into the primary float chamber (220).

3. The autofeed mechanism (10) of claim 1, further including a ball support extending from the inlet chamber base surface to form the support surface at a support length distance, and wherein an orthogonal distance from the inlet chamber base surface (212) to the primary seat channel distal end (243) is substantially equal to a total of the support length (217), the primary ball diameter (232), and the stem length (255), and a float portion base surface (259) is formed with at least one flow channel (260) to facilitate the flow of fluid from the primary seat channel (242) into the primary float chamber (220).

4. The autofeed mechanism (10) of claim 1, wherein the stem cross sectional area (256) is at least ten percent less than the primary seat channel opening cross sectional area (246).

5. The autofeed mechanism (10) of claim 1, wherein the primary seat channel opening cross sectional area (246) at the primary seat channel proximal end (244) is at least ten percent less than the maximum cross sectional area of the primary ball (230).

6. The autofeed mechanism (10) of claim 1, wherein the support surface is substantially collinear with the center of the primary ball (230) and with a central axis of the stem portion (252).

7. The autofeed mechanism (10) of claim 1, wherein the weight of the primary float (250) is greater than a buoyant force produced by the primary ball (230) being totally submerged in the fluid resulting in the primary float (250) acting on the primary ball (230) and keeping the primary ball (230) against the support surface and away from the primary seat channel proximal end (244) when the primary inlet chamber (210) is filled with the fluid until the predetermined primary fluid level (500) is reached.

8. The autofeed mechanism (10) of claim 1, further including:
a secondary housing (300) in the body (100), having a secondary inlet chamber (310) with an inlet chamber base surface (312), and a secondary float chamber (320), wherein the secondary inlet chamber (310) has a secondary fluid inlet (370), through which the fluid enters the secondary inlet chamber (310), and the secondary float chamber (320) has a secondary fluid exit (380), through which the fluid exits the secondary float chamber (320);
a secondary seat (340) facilitating fluid communication between the secondary inlet chamber (310) and the secondary float chamber (320) having a secondary seat channel (342) with a distal end (343) open to the secondary float chamber (320), a proximal end (344) open to the secondary inlet chamber (310), wherein the distance from the distal end (343) to the proximal end (344) defines a secondary channel length (349), and an opening cross sectional area (346);
a secondary float (350) having a float portion (358), located in the secondary float chamber (320), and a stem portion (352) projecting toward the secondary seat (340) and substantially parallel with the secondary seat channel (342), wherein the secondary float chamber (320) is configured to allow the secondary float (350) to move freely in the primary float chamber (220) when acted upon, and wherein the stem portion (352) cooperates with the secondary seat (340) so that it may move within the secondary seat channel (342) with the movement of the secondary float (350), and the stem portion (352) has a distal end (353) at the connection to the float portion (358) and a proximal end (354) nearest the secondary seat (340) with the distance between the distal end (353) and the proximal end (354) defining a stem length (355), and the stem portion (352) has a stem cross sectional area (356) less than the secondary seat channel opening cross sectional area (346) thereby permitting the fluid to flow through secondary seat channel (342) when the stem portion (352) is in the secondary seat channel (342);
a secondary ball (330), having a diameter (332), located in the secondary inlet chamber (310) and configured such that the center of the secondary ball (330) is substantially collinear with a central axis of the stem portion (352), and the secondary ball (330) is acted upon by the secondary float stem portion (352) thereby forcing the secondary ball (330) against a ball support (314) extending from the inlet chamber base surface (312) a support length (317) distance thus allowing fluid entering the primary inlet chamber (310) to pass the secondary ball (330) and exit to the secondary float chamber (320) and the secondary fluid exit (380) by passing through the secondary seat (340) around the stem portion (352), until the fluid level reaches a predetermined secondary fluid elevation (600) thereby reducing the action of the stem portion (352) on the secondary ball (330) and allowing the secondary ball (330) to float away from the ball support (314) and seal the secondary seat channel proximal end (344) thereby preventing the fluid from flowing from the secondary inlet chamber (310) to the secondary float chamber (320) thus stopping the flow of fluid.

9. The autofeed mechanism (10) of claim 8, wherein the predetermined secondary fluid level (600) is higher than the predetermined primary fluid level (500) thereby providing a visual indication that the primary ball (230) is malfunctioning.

10. The autofeed mechanism (10) of claim 8, wherein the orthogonal distance from the secondary inlet chamber base surface (312) to the secondary seat channel distal end (343) is less than the total of the secondary support length (317), the secondary ball diameter (332), and the secondary stem length (355) thereby ensuring the presence of a gap between the secondary seat channel proximal end (344) and a secondary float portion base surface (359) to facilitate the flow of fluid into the secondary float chamber (320).

11. An autofeed mechanism for a heated humidifier chamber (10) for controlling the flow of a fluid, comprising:
1) a body (100) defining a primary housing (200) and a secondary housing (300), wherein:
   a) the primary housing (200) has a primary inlet chamber (210) with a primary inlet chamber base surface (212), and a primary float chamber (220), wherein the primary inlet chamber (210) has a primary fluid inlet (270), through which the fluid enters the primary inlet chamber (210), and the primary float chamber (220) has a primary fluid exit (280), through which the fluid exits the primary float chamber (220), and
   b) the secondary housing (300) has a secondary inlet chamber (310) with a secondary inlet chamber base surface (312), and a secondary float chamber (320), wherein the secondary inlet chamber (310) has a secondary fluid inlet (370) in fluid communication with the primary fluid exit (280), through which the fluid enters the secondary inlet chamber (310), and the secondary float chamber (320) has a secondary fluid exit (380), through which the fluid exits the secondary float chamber (320),
2) a primary seat (240) facilitating fluid communication between the primary inlet chamber (210) and the primary float chamber (220) having a primary seat channel (242) with a primary channel distal end (243) open to the primary float chamber (220), a primary channel proximal end (244) open to the primary inlet chamber (210), wherein the distance from the primary channel distal end (243) to the primary channel proximal end (244) defines a primary channel length (245), and a primary opening cross sectional area (246);
3) a secondary seat (340) facilitating fluid communication between the secondary inlet chamber (310) and the secondary float chamber (320) having a secondary seat channel (342) with a secondary channel distal end (343) open to the secondary float chamber (320), a secondary channel proximal end (344) open to the secondary inlet chamber (310), wherein the distance from the secondary channel distal end (343) to the secondary channel proximal end (344) defines a secondary channel length (349), and a secondary opening cross sectional area (346);
4) a primary float (250) having a primary float portion (258), located in the primary float chamber (220), and a primary stem portion (252) projecting toward the primary seat (240) and substantially parallel with the primary seat channel (242), wherein the primary float chamber (220) is configured to allow the primary float (250) move freely in the primary float chamber (220) when acted upon, and wherein the primary stem portion (252) cooperates with the primary seat (240) 50 that it may move within the primary seat channel (242) with the movement of the primary float (250), and the primary stem portion (252) has a primary distal end (253) at the connection to the primary float portion (258) and a primary proximal end (254) nearest the primary seat (240) with the distance between the primary distal end (253) and the primary proximal end (254) defining a primary stem length (255), wherein the primary stem length (255) is a statically fixed distance and the primary stem portion (252) has a primary stem cross sectional area (256) less than the primary seat channel opening cross sectional area (246) thereby permitting the fluid to flow through primary seat channel (242) when the primary stem portion (252) is in the primary seat channel (242);
5) a secondary float (350) having a secondary float portion (358), located in the secondary float chamber (320), and a secondary stem portion (352) projecting toward the secondary seat (340) and substantially parallel with the secondary seat channel (342), wherein the secondary float chamber (320) is configured to allow the secondary float (350) to move freely in the primary float chamber (220) when acted upon, and wherein the secondary stem portion (352) cooperates with the secondary seat (240) so that it may move within the secondary seat channel (342) with the movement of the secondary float (350), and the secondary stem portion (352) has a secondary distal end (353) at the connection to the secondary float portion (358) and a secondary proximal end (354) nearest the secondary seat (340) with the distance between the secondary distal end (353) and the secondary proximal end (354) defining a secondary stem length (355), and the secondary stem portion (352) has a secondary stem cross sectional area (356) less than the secondary seat channel opening cross sectional area (346) thereby permitting the fluid to flow through secondary seat channel (342) when the secondary stem portion (352) is in the secondary seat channel (342);
6) a primary ball (230), having a primary diameter (232), located in the primary inlet chamber (210) and configured such that the center of the primary ball (230) is substantially collinear with a central axis of the primary stem portion (252), and the primary ball (230) is acted upon by the primary float stem portion (252) thereby forcing the primary ball (230) against a primary ball support (214) extending from the primary inlet chamber base surface (212) a primary support length (217) distance thus allowing fluid entering the primary inlet chamber (210) to pass the primary ball (230) and exit to the primary float chamber (220) and the primary fluid exit (280) by passing through the primary seat (240) around the primary stem portion (252), until the fluid level reaches a predetermined primary fluid elevation (500) thereby reducing the action of the primary stem portion (252) on the primary ball (230) and allowing the primary ball (230) to float away from the primary ball support (214) and seal the primary seat channel proximal end (244) thereby preventing the fluid from flowing from the primary inlet chamber (210) to the primary float chamber (220) thus stopping the flow of fluid; and
7) a secondary ball (330), having a secondary diameter (332), located in the secondary inlet chamber (310) and configured such that the center of the secondary ball (330) is substantially collinear with a central axis of the secondary stem portion (352), and the secondary ball (330) is acted upon by the secondary float stem portion (352) thereby forcing the secondary ball (330) against a secondary ball support (314) extending from the secondary inlet chamber base surface (312) a secondary support length (317) distance thus allowing fluid entering the secondary inlet chamber (310) to pass the secondary ball (330) and exit to the secondary float chamber (220) and the secondary fluid exit (380) by passing through the secondary seat (340) around the secondary stem portion (352), until the fluid level reaches a predetermined secondary fluid elevation (600) thereby reducing the action of the secondary stem portion (352) on the secondary ball (330) and allowing the secondary ball (330) to float away from the secondary ball support (314) and seal the secondary seat channel proximal end (344) thereby preventing the fluid from flowing from the secondary inlet chamber (310) to the secondary float chamber (220) thus stopping the flow of fluid.

12. The autofeed mechanism (10) of claim 11, wherein the orthogonal distance from the primary inlet chamber base surface (212) to the primary seat channel distal end (243) is less than the total of the primary support length (217), the primary ball diameter (232), and the primary stem length (255) thereby ensuring the presence of a gap between the primary seat channel proximal end (244) and a primary float portion base surface (259) to facilitate the flow of fluid into the primary float chamber (220), and the orthogonal distance from the secondary inlet chamber base surface (312) to the secondary seat channel distal end (343) is less than the total of the secondary support length (317), the secondary ball diameter (332), and the secondary stem length (355) thereby ensuring the presence of a gap between the secondary seat channel proximal end (344) and a secondary float portion base surface (359) to facilitate the flow of fluid into the secondary float chamber (320).

13. The autofeed mechanism (10) of claim 11, wherein the primary stem cross sectional area (256) is at least ten percent less than the primary seat channel opening cross sectional area (246), and the secondary stem cross sectional area (356) is at least ten percent less than the secondary seat channel opening cross sectional area (346).

14. The autofeed mechanism (10) of claim 11, wherein the primary seat channel opening cross sectional area (246) at the primary seat channel proximal end (244) is at least ten percent less than the maximum cross sectional area of the primary ball (230), and the secondary seat channel opening cross sectional area (346) at the secondary seat channel proximal end (344) is at least ten percent less than the maximum cross sectional area of the secondary ball (330).

15. The autofeed mechanism (10) of claim 11, wherein the primary ball support (214) is substantially collinear with the center of the primary ball (230) and with a central axis of the primary stem portion (252), and the secondary ball support (314) is substantially collinear with the center of the secondary ball (330) and with a central axis of the secondary stem portion (352).

16. The autofeed mechanism (10) of claim 11, wherein the weight of the primary float (250) is greater than a buoyant force produced by the primary ball (230) being totally submerged in the fluid resulting in the primary float (250) acting on the primary ball (230) and keeping the primary ball (230) against the primary ball support (214) and away from the primary seat channel proximal end (244) when the primary inlet chamber (210) is filled with the fluid until the predetermined primary fluid level (500) is reached, and the weight of the secondary float (350) is greater than a buoyant force produced by the secondary ball (330) being totally submerged in the fluid resulting in the secondary float (350) acting on the secondary ball (330) and keeping the secondary ball (330) against the secondary ball support (314) and away from the secondary seat channel proximal end (344) when the secondary inlet chamber (310) is filled with the fluid until the predetermined secondary fluid level (600) is reached.

17. The autofeed mechanism (10) of claim 11, wherein the predetermined secondary fluid level (600) is higher than the predetermined primary fluid level (500) thereby providing a visual indication that the primary ball (230) is malfunctioning.

18. The autofeed mechanism (10) of claim 11, wherein the secondary fluid exit (380) is higher in elevation than the primary fluid exit (280).

19. The autofeed mechanism of claim 11, wherein the secondary support length (317) is greater than the primary support length (217).

20. An autofeed mechanism for a heated humidifier chamber (10) for controlling the flow of a fluid, comprising:
1) a body (100) defining a primary housing (200) and a secondary housing (300), wherein:
   a) the primary housing (200) has a primary inlet chamber (210) with a primary inlet chamber base surface (212), and a primary float chamber (220), wherein the primary inlet chamber (210) has a primary fluid inlet (270), through which the fluid enters the primary inlet chamber (210), and the primary float chamber (220) has a primary fluid exit (280), through which the fluid exits the primary float chamber (220), and
   b) the secondary housing (300) has a secondary inlet chamber (310) with a secondary inlet chamber base surface (312), and a secondary float chamber (320), wherein the secondary inlet chamber (310) has a secondary fluid inlet (370) in fluid communication with the primary fluid exit (280), through which the fluid enters the secondary inlet chamber (310), and the secondary float chamber (320) has a secondary fluid exit (380), higher in elevation than the primary fluid exit (280), through which the fluid exits the secondary float chamber (320),
2) a primary seat (240) facilitating fluid communication between the primary inlet chamber (210) and the primary float chamber (220) having a primary seat channel (242) with a primary channel distal end (243) open to the primary float chamber (220), a primary channel proximal end (244) open to the primary inlet chamber (210), wherein the distance from the primary channel distal end (243) to the primary channel proximal end (244) defines a primary channel length (245), and a primary opening cross sectional area (246);
3) a secondary seat (340) facilitating fluid communication between the secondary inlet chamber (310) and the secondary float chamber (320) having a secondary seat channel (342) with a secondary channel distal end (343) open to the secondary float chamber (320), a secondary channel proximal end (344) open to the secondary inlet chamber (310), wherein the distance from the secondary channel distal end (343) to the secondary channel proximal end (344) defines a secondary channel length (345), and a secondary opening cross sectional area (346);
4) a primary float (250) having a primary float portion (258), located in the primary float chamber (220), and a primary stem portion (252) projecting toward the primary seat (240) and substantially parallel with the primary seat channel (242), wherein the primary float chamber (220) is configured to allow the primary float (250) to move freely in the primary float chamber (220) when acted upon, and wherein the primary stem portion (252) cooperates with the primary seat (240) SO that it may move within the primary seat channel (242) with the movement of the primary float (250), and the primary stem portion (252) has a primary distal end (253) at the connection to the primary float portion (258) and a primary proximal end (254) nearest the primary seat (240) with the distance between the primary distal end (253) and the primary proximal end (254) defining a primary stem length (255), and the primary stem portion (252) has a primary stem cross sectional area (256) at least ten percent less than the primary seat channel opening cross sectional area (246) thereby permitting the fluid to flow through primary seat channel (242) when the primary stem portion (252) is in the primary seat channel (242); wherein the primary stem cross sectional area (256) is at least ten percent less than the primary seat channel opening cross sectional area (246)

5) a secondary float (350) having a secondary float portion (358), located in the secondary float chamber (320), and a secondary stem portion (352) projecting toward the secondary seat (340) and substantially parallel with the secondary seat channel (342), wherein the secondary float chamber (320) is configured to allow the secondary float (350) to move freely in the primary float chamber (220) when acted upon, and wherein the secondary stem portion (352) cooperates with the secondary seat (240) so that it may move within the secondary seat channel (342) with the movement of the secondary float (350), and the secondary stem portion (352) has a secondary distal end (353) at the connection to the secondary float portion (358) and a secondary proximal end (354) nearest the secondary seat (340) with the distance between the secondary distal end (353) and the secondary proximal end (354) defining a secondary stem length (355), and the secondary stem portion (352) has a secondary stem cross sectional area (356) at least ten percent less than the secondary seat channel opening cross sectional area (346) thereby permitting the fluid to flow through secondary seat channel (342) when the secondary stem portion (352) is in the secondary seat channel (342);

6) a primary ball (230), having a primary diameter (232) and a maximum cross sectional area at least ten percent greater than the primary seat channel opening cross sectional area (246) at the primary seat channel proximal end (244), located in the primary inlet chamber (210) and configured such that the center of the primary ball (230) is substantially collinear with a central axis of the primary stem portion (252), and the primary ball (230) is acted upon by the primary float stem portion (252) thereby forcing the primary ball (230) against a primary ball support (214) extending from the primary inlet chamber base surface (212) a primary support length (217) distance, and being substantially collinear with the center of the primary ball (230) and with a central axis of the primary stem portion (252), thus allowing fluid entering the primary inlet chamber (210) to pass the primary ball (230) and exit to the primary float chamber (220) and the primary fluid exit (280) by passing through the primary seat (240) around the primary stem portion (252), until the fluid level reaches a predetermined primary fluid elevation (500) thereby reducing the action of the primary stem portion (252) on the primary ball (230) and allowing the primary ball (230) to float away from the primary ball support (214) and seal the primary seat channel proximal end (244) thereby preventing the fluid from flowing from the primary inlet chamber (210) to the primary float chamber (220) thus stopping the flow of fluid;

7) a secondary ball (330), having a secondary diameter (332) and a maximum cross sectional area at least ten percent greater than the secondary seat channel opening cross sectional area (346) at the secondary seat channel proximal end (344), located in the secondary inlet chamber (310) and configured such that the center of the secondary ball (330) is substantially collinear with a central axis of the secondary stem portion (352), and the secondary ball (330) is acted upon by the secondary float stem portion (352) thereby forcing the secondary ball (330) against a secondary ball support (314) extending from the secondary inlet chamber base surface (312) a secondary support length (317) distance, and being substantially collinear with the center of the secondary ball (330) and with a central axis of the secondary stem portion (352), thus allowing fluid entering the secondary inlet chamber (310) to pass the secondary ball (330) and exit to the secondary float chamber (220) and the secondary fluid exit (380) by passing through the secondary seat (340) around the secondary stem portion (352), until the fluid level reaches a predetermined secondary fluid elevation (600) thereby reducing the action of the secondary stem portion (352) on the secondary ball (330) and allowing the secondary ball (330) to float away from the secondary ball support (314) and seal the secondary seat channel proximal end (344) thereby preventing the fluid from flowing from the secondary inlet chamber (310) to the secondary float chamber (220) thus stopping the flow of fluid; and 8) wherein an orthogonal distance from the primary inlet chamber base surface (212) to the primary seat channel distal end (243) is substantially equal to a total of the primary support length (217), the primary ball diameter (232), and the primary stem length (255), a primary float portion base surface (259) is formed with at least one flow channel (260) to facilitate the flow of fluid from the primary seat channel (242) into the primary float chamber (220), and an orthogonal distance from the secondary inlet chamber base surface (312) to the secondary seat channel distal end (343) is less than the total of the secondary support length (317), the secondary ball diameter (332), and the secondary stem length (355) thereby ensuring the presence of a gap between the secondary seat channel proximal end (344) and a secondary float portion base surface (359) to facilitate the flow of fluid into the secondary float chamber (320).

21. The autofeed mechanism (10) of claim 20, wherein the weight of the primary float (250) is greater than a buoyant force produced by the primary ball (230) being totally submerged in the fluid resulting in the primary float (250) acting on the primary ball (230) and keeping the primary ball (230) against the primary ball support (214) and away from the primary seat channel proximal end (244) when the primary inlet chamber (210) is filled with the fluid until the predetermined primary fluid level (500) is reached, and the weight of the secondary float (350) is greater than a buoyant force produced by the secondary ball (330) being totally submerged in the fluid resulting in the secondary float (350) acting on the secondary ball (330) and keeping the secondary ball (330) against the secondary ball support (314) and away from the secondary seat channel proximal end (344) when the secondary inlet chamber (310) is filled with the fluid until the predetermined secondary fluid level (600) is reached.

* * * * *

UNITED STATES PATENT AND TRADEMARK OFFICE
CERTIFICATE OF CORRECTION

| | |
|---|---|
| PATENT NO. | : 7,614,420 B2 |
| APPLICATION NO. | : 11/405341 |
| DATED | : November 10, 2009 |
| INVENTOR(S) | : Rustad et al. |

It is certified that error appears in the above-identified patent and that said Letters Patent is hereby corrected as shown below:

Column 8, line 20, in claim 1, delete "50" and insert in place thereof --so--.

Column 10, line 25, in claim 8, delete "349," and insert in place thereof --(345),--.

Column 11, line 67, in claim 11, delete "50" and insert in place thereof --so--.

Column 13, line 40, in claim 14, delete "claim 11 ," and insert in place thereof --claim 11,--.

Column 14, line 67, in claim 20, delete "SO" and insert in place thereof --so--.

Column 15, line 16, in claim 20, after "(246)" insert --;--.

Column 15, line 45, in claim 20, delete "bail" and insert in place thereof --ball--.

Signed and Sealed this

Second Day of February, 2010

David J. Kappos
*Director of the United States Patent and Trademark Office*